(12) United States Patent
Jessen et al.

(10) Patent No.: US 6,271,437 B1
(45) Date of Patent: Aug. 7, 2001

(54) SOYBEAN GENE PROMOTERS

(75) Inventors: Holly J. Jessen, Chanhassen, MN (US); Terry E. Meyer, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/311,042

(22) Filed: May 13, 1999

Related U.S. Application Data

(60) Provisional application No. 60/085,823, filed on May 18, 1998.

(51) Int. Cl.$^7$ ............... C12N 5/04; C12N 15/29; C12N 15/82; A01H 5/00; A01H 5/10

(52) U.S. Cl. ............... 800/278; 800/279; 800/287; 800/298; 800/295; 800/320; 800/312; 800/320.1; 435/69.1; 435/419; 435/468; 435/252.3; 435/320.1; 536/23.1; 536/24.1; 536/23.6

(58) Field of Search ............... 800/279, 287, 800/278, 298, 312, 320.1, 320, 295; 435/69.1, 468, 419, 252.3, 320.1; 536/23.1, 24.1, 23.6

(56) References Cited

U.S. PATENT DOCUMENTS

| | | | |
|---|---|---|---|
| 5,491,081 | * | 2/1996 | Webb ............... 435/172.3 |
| 5,770,786 | * | 6/1998 | Sijmons ............... 800/200 |

FOREIGN PATENT DOCUMENTS

| | | |
|---|---|---|
| WO 92/04453 | 3/1992 | (WO) . |
| WO 92/21757 | * 12/1992 | (WO) . |
| WO 95/20669 | 11/1995 | (WO) . |
| WO 97/46692 | 12/1997 | (WO) . |
| WO 98/12335 | 3/1998 | (WO) . |
| WO 98/22599 | 5/1998 | (WO) . |

OTHER PUBLICATIONS

Sambrook, J. et al. Molecular Cloning, A Laboratory Manual, 2nd edition, Cold Spring Harbor Lab., 1989.*

Goddijin et al., Differential Gene Expression in Nematode–Induced Feeding Structures of Transgenic plants Harbouring Promoter–gusA Fusion Constructs, *The Plant Journal*, 1993, pp. 863–873, vol. 4(5).

Webb et al., Genetic Mapping of Soybean Cyst Nematode Race–3 Resistance locl in the Soybean Pl 437.654, *Theor Appl Genet*, 1995, pp. 574–581, vol. 91.

Barthels et al., Regulatory Sequences of Arabidopsis Drive Reporter Gene Expression in Nematode Feeding Structures, *The Plant Cell*, Dec. 1997, pp. 2119–2134, vol. 9, American Society of Plant Physiologist.

Shoemaker et al., Glycine max cDNA Clone, Database Embl Nucleotide and Protein Sequences, Jun. 18, 1999, Genome Systems Clone ID: Gm–c1009–279 5' similare to TR:004203 004203 HS1PRO–1 Related, Protein Isolog; mRNA sequence XP002118494; Hinxton, GB: AC=AI736522.

Ward et al., Chemical Regulation of Transgene Expression in Plants, Plant Molecular Biology, 1993, pp. 361–366, vol. 22, Kluwer Academic Publishers, Belgium.

* cited by examiner

Primary Examiner—David T. Fox
Assistant Examiner—Medina A. Ibrahim
(74) Attorney, Agent, or Firm—Alston & Bird LLP

(57) ABSTRACT

The present invention provides compositions and methods for regulating expression of heterologous nucleotide sequences in a plant. Compositions are novel nucleotide sequences for promoters isolated from genes encoding soybean cyst nematode genes. A method for expressing a heterologous nucleotide sequence in a plant using the promoter sequences disclosed herein is provided. The method comprises transforming a plant cell with a heterologous nucleotide sequence operably linked to the promoters of the present invention and regenerating a stably transformed plant from the transformed plant cell.

48 Claims, 3 Drawing Sheets

SOYBEAN GENE PROMOTERS

CROSS-REFERENCE

This application claims the benefit of U.S. Provisional Application Ser. No. 60/085,823, filed May 18, 1998.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Thus, where continuous expression is desired throughout the cells of a plant, constitutive promoters are utilized. In contrast, where gene expression in response to a stimulus is desired, inducible promoters are the regulatory element of choice. Where expression in particular organs is desired, tissue specific promoters are utilized. Additional regulatory sequences upstream and/or downstream from the core promoter sequence may be included in expression constructs of transformation vectors to bring about varying levels of constitutive or inducible expression of heterologous nucleotide sequences in a transgenic plant.

Frequently it is desirable to have constitutive expression of a DNA sequence throughout the cells of an organism. For example, increased resistance of a plant to infection by soil- and air-borne pathogens might be accomplished by genetic manipulation of the plant's genome to comprise a constitutive promoter operably linked to a heterologous pathogen-resistance gene such that pathogen-resistance proteins are continuously expressed throughout the plant's tissues.

Alternatively, it might be desirable to inhibit expression of a native DNA sequence within a plant's tissues to achieve a desired phenotype. In this case, such inhibition might be accomplished with transformation of the plant to comprise a constitutive promoter operably linked to an antisense nucleotide sequence, such that constitutive expression of the antisense sequence produces an RNA transcript that interferes with translation of the mRNA of the native DNA sequence.

Thus, isolation and characterization of promoters that can serve as regulatory regions for expression of heterologous nucleotide sequences of interest are needed for genetic manipulation of plants to exhibit specific phenotypic traits.

SUMMARY OF THE INVENTION

Compositions and methods for regulating expression of heterologous nucleotide sequences in a plant are provided. The compositions comprise novel nucleotide sequences for plant promoters, more particularly promoters isolated from and having sequence similarity to soybean promoters of a soybean cyst nematode resistance gene as well as promoters driving allelic variants of the resistance gene. Methods for expressing a heterologous nucleotide sequence in a plant using the promoter sequences disclosed herein are provided. The method comprises transforming a plant cell with a transformation vector that comprises a heterologous nucleotide sequence operably linked to one of the plant promoters of the present invention and regenerating a stably transformed plant from the transformed plant cell.

DETAILED DESCRIPTION OF THE INVENTION

Figure 1:
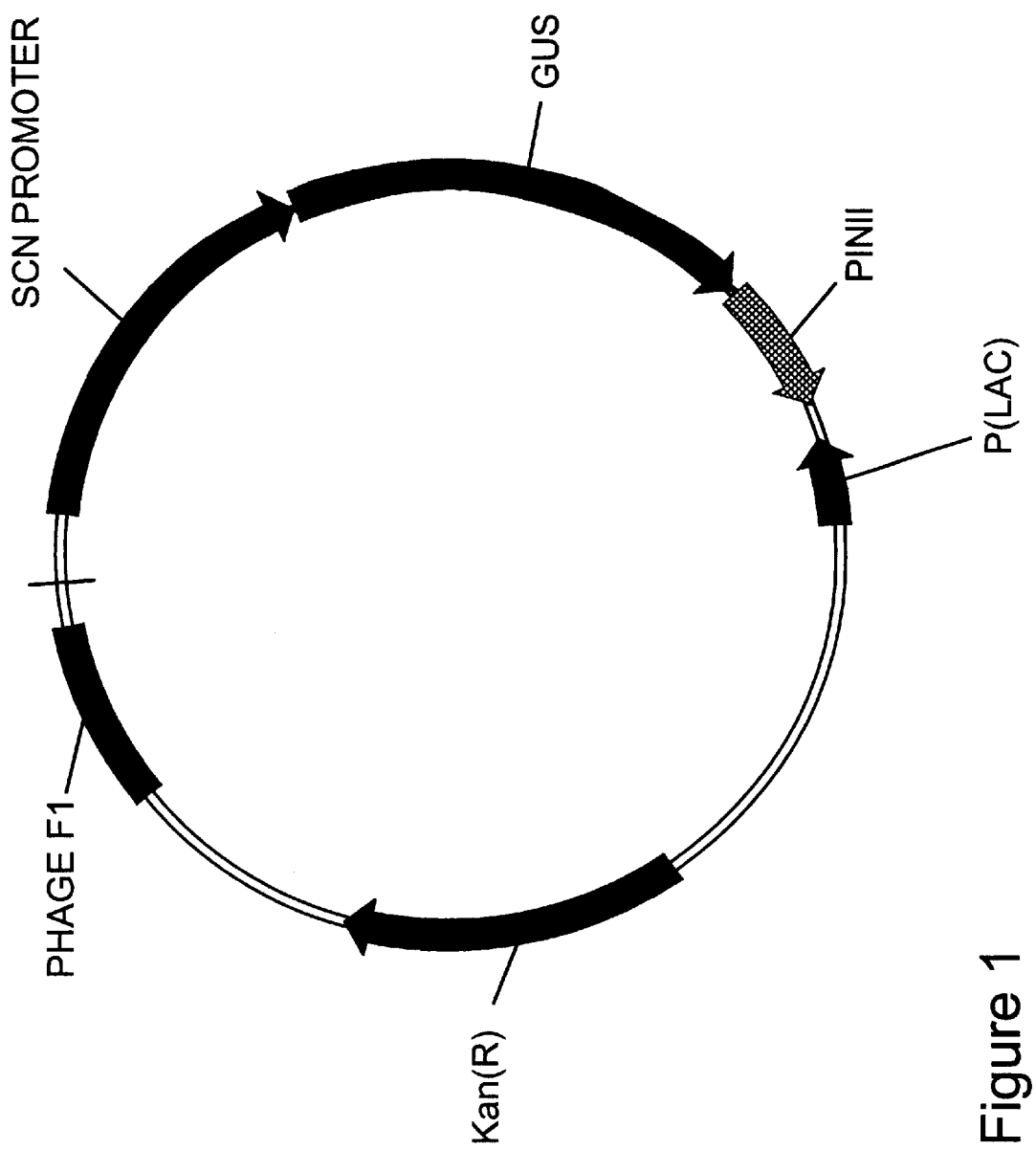
FIG. 1 schematically illustrates the plasmid vector comprising the GUS gene operably linked to a promoter of the present invention.

Compositions of the present invention are novel nucleotide sequences for plant promoters, more particularly promoters for the genes encoding soybean cyst nematode resistance gene and allelic variants thereof. Particularly, the promoters from genes related to soybean cyst nematode resistance gene and allelic variants that result in a susceptible phenotype are provided. The nucleotide sequences of the promoters from the soybean cyst nematode genes related to resistance and susceptibility are set forth in SEQ ID NOs: 1 and 2, respectively. In particular, the present invention provides for isolated nucleic acid molecules comprising nucleotide sequences encoding the DNA sequences deposited in a bacterial host as ATCC Accession No. 209689, and variants and fragments thereof. The promoters for these maize genes were isolated from the 5' untranslated region flanking their respective transcription initiation sites. Methods for isolation of promoter regions are well known in the art. The specific method used to obtain the promoters of the present invention is described in Example 1 below.

A plasmid containing the promoter nucleotide sequences of the invention was deposited with American Type Culture Collection (ATCC), Manassas, Va., on Mar. 18, 1998, and assigned Accession No. 209689. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The invention encompasses isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

By "soybean cyst nematode resistance gene" is intended a gene that when expressed in a soybean plant contributes to resistance to soybean cyst nematode. Alternatively, a soybean cyst nematode gene may be an allelic variant of the resistance gene particularly variants resulting in a susceptible phenotype.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the sequences for the promoter regions disclosed herein, it is within the state of the art to isolate and identify further regulatory elements in the 5' untranslated region upstream from the particular promoter regions identified herein. See particularly Australian Patent No. AU-A-77751/94 and U.S. Pat. Nos. 5,466,785 and 5,635,618.

The promoter sequences of the present invention, when operably linked to a heterologous nucleotide sequence of interest and inserted into a transformation vector, drive expression of the heterologous nucleotide sequence in the cells of a plant stably transformed with this vector. By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host. The invention additionally encompasses expression of the homologous coding sequences of the promoters, particularly the coding sequences related to the resistance phenotype. The expression of the homologous coding sequences will alter the phenotype of the transformed plant or plant cell.

The isolated promoter sequences of the present invention can be modified to provide for a range of expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the general nature of expression may be changed. Generally, at least about 20 nucleotides of an isolated promoter region will be used to drive expression of a nucleotide sequence.

It is recognized that to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

Modifications of the isolated promoter sequences of the present invention can provide for a range of expression. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

The nucleotide sequences for the promoters of the present invention may be the naturally occurring sequences or any sequence having substantial homology. By "substantial homology" is intended a sequence exhibiting substantial functional and structural equivalence with the native or naturally occurring sequence. Any functional or structural differences between substantially homologous sequences do not affect the ability of the sequence to function as a promoter as disclosed in the present invention. Thus, the promoter of the present invention will direct expression of an operably linked heterologous nucleotide sequence. Two promoter nucleotide sequences are considered substantially homologous when they have at least about 50%, 60%, 70%, preferably at least about 80%, more preferably at least about 90%, still more preferably at least about 95% sequence homology.

Fragments and variants of the disclosed nucleotide sequences are also encompassed by the present invention. By "fragment" is intended a portion of the nucleotide sequence. Fragments of a nucleotide sequence may retain biological activity and hence promote expression of an operably linked nucleotide sequence. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length of a nucleotide sequence of the invention.

Thus, a fragment of a promoter sequence disclosed herein may encode a biologically active portion of a promoter, or it may be a fragment that can be used as a hybridization probe or PCR primer using methods disclosed below. A biologically active portion of a promoter can be prepared by isolating a portion of one of the promoter nucleotide sequences of the invention and assessing the activity of the fragment. Nucleic acid molecules that are fragments of a promoter nucleotide sequence comprise at least 15, 20, 50, 75, 100, 150, 200, 250, 300, 350, 400, 450, 500, 550, 600, 650, 700, 800, 900, or 1,000 nucleotides, or up to the number of nucleotides present in a full-length promoter nucleotide sequence disclosed herein (for example, 1692 or 1069 nucleotides for SEQ ID NOs: 1 or 2, respectively).

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis and a procedure such as DNA "shuffling", are encompassed by the compositions of the present invention.

By "variants" is intended substantially similar sequences. Naturally occurring variants of the disclosed promoter sequences can be identified with the use of well-known molecular biology techniques, as, for example, with PCR and hybridization techniques as outlined below. Variant nucleotide sequences also include synthetically derived nucleotide sequences, such as those generated, for example, by using site-directed mutagenesis, but which still exhibit promoter activity. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Generally, nucleotide sequence variants of the invention will have at least 40%, 50%, 60%, 70%, generally, 80%, preferably 85%, 90%, up to 95%, 98% sequence identity to its respective native or reference promoter nucleotide sequence.

Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

Biologically active variants of the promoter sequences should retain promoter activity and thus promote expression of an operably linked heterologous nucleotide sequence. Promoter activity may be measured by Northern blot analysis. See, for example, Sambrook et al. (1989) *Molecular Cloning: A Laboratory Manual* (2d ed., Cold Spring Harbor Laboratory Press, Plainview, N.Y.), herein incorporated by reference.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire promoter sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols. A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the poromoter sequences of the invention. Methods for preparation of probes for hybridization and for construction of cDNA and genomic libraries are generally known in the art and are disclosed in Sambrook et al. (1 989) *Molecular Cloning: A Laboratory Manual* (2d ed., Cold Spring Harbor Laboratory Press, Plainview, N.Y.).

For example, the entire promoter sequences disclosed herein, or one or more portions thereof, may be used as a probe capable of specifically hybridizing to corresponding promoter sequences. To achieve specific hybridization under a variety of conditions, such probes include sequences that are unique among promoter sequences and are preferably at least about 10 nucleotides in length, and most preferably at least about 20 nucleotides in length. Such probes may be used to amplify corresponding promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1 % of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology— Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y. ).

In general, sequences that have promoter activity and hybridize to the promoter sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment.

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described above using standard or default parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

The nucleotide sequences for the promoters of the present invention, as well as variants and fragments thereof, are useful in the genetic manipulation of any plant when operably linked with a heterologous nucleotide sequence whose expression is to be controlled to achieve a desired phenotypic response. By "operably linked" is intended the transcription or translation of the heterologous nucleotide sequence is under the influence of the promoter sequence. In this manner, the nucleotide sequences for the promoters of the invention are provided in expression cassettes along with nucleotide sequences of interest for expression in the plant of interest.

Such expression cassettes will comprise a transcriptional initiation region comprising one of the promoter nucleotide sequences of the present invention, or variants or fragments thereof, operably linked to the heterologous nucleotide sequence whose expression is to be controlled by the promoters disclosed herein. Such an expression cassette is provided with a plurality of restriction sites for insertion of the nucleotide sequence to be under the transcriptional regulation of the regulatory regions. The expression cassette may additionally contain selectable marker genes.

The transcriptional cassette will include in the 5'-to-3' direction of transcription, a transcriptional and translational initiation region, a heterologous nucleotide sequence of interest, and a transcriptional and translational termination region functional in plant cells. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens,* such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The expression cassette comprising the promoter sequence of the present invention operably linked to a heterologous nucleotide sequence may also contain at least one additional nucleotide sequence for a gene to be cotransformed into the organism. Alternatively, the additional sequence(s) can be provided on another expression cassette.

Where appropriate, the heterologous nucleotide sequence whose expression is to be under the control of the promoter sequence of the present invention and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak and Sarnow (1991) *Nature* 353:90–94); untranslated leader from the coat protein mRNA of alfalfa mosaic virus (AMV RNA 4) (Jobling and Gehrke (1987) *Nature* 325:622–625); tobacco mosaic virus leader (TMV) (Gallie et al. (1989) *Molecular Biology of RNA,* pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In those instances where it is desirable to have the expressed product of the heterologous nucleotide sequence directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The promoters may be used to drive reporter genes or selectable marker genes. Examples of suitable reporter genes known in the art can be found in, for example, Jefferson et al. (1991) in *Plant Molecular Biology Manual,* ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; and Kain et al. (1995) *BioTechniques* 19:650–655; and Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sufonamide (Guerineau et al. (1990) *Plant Mol Biol.* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, such examples as GUS (b-glucoronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.*15(19):8115 and Luehrsen et al. (1992) *Methods Enszymol.* 216:397–414), and the maize genes encoding for anthocyanin production (Ludwig et al. (1990) *Science* 247:449).

The expression cassette comprising the particular promoter sequence of the present invention operably linked to a heterologous nucleotide sequence of interest can be used to transform any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues,* ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The promoter sequences and methods disclosed herein are useful in regulating expression of any heterologous nucleotide sequence in a host plant. Thus, the heterologous nucleotide sequence operably linked to the promoters disclosed herein may be a structural gene encoding a protein of interest. Examples of such heterologous genes include, but are not limited to, genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997; Ser. No. 08/824,379, filed Mar. 26, 1997; Ser. No. 08/824,382, filed Mar. 26, 1997; and U.S. Pat. No. 5,703,409; herein incorporated by reference. Another example is lysine and/or sulfur rich seed protein encoded by the soybean 2S albumin described in U.S. application Ser. No. 08/618,911, filed Mar. 20, 1996, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and PCT/US97/20441, filed Oct. 31, 1997, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs,* ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins, described in U.S. application Ser. No. 08/838,763 (filed Apr. 10, 1997), Ser. No. 08/824,379 (filed Mar. 26, 1997), and Ser. No. 08/824,382 (filed Mar. 26, 1997), and U.S. Pat. No. 5,703,409, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837–5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Alternatively, the heterologous nucleotide sequence operably linked to one of the promoters disclosed herein may be an antisense sequence for a targeted gene. Thus, antisense constructions, complementary to at least a portion of the messenger RNA (mRNA) for the heterologous nucleotide sequence can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used. When delivered into a plant cell, expression of the antisense DNA sequence prevents normal expression of the DNA nucleotide sequence for the targeted gene. In this manner, production of the native protein encoded by the targeted gene is inhibited to achieve a desired phenotypic response. Thus the promoter is linked to antisense DNA sequences to reduce or inhibit expression of a native protein in the plant.

The following examples are offered by way of illustration and not by way of limitation.

Experimental

Promoter regions for a soybean cyst nematode (SCN) resistance gene and an allelic variant of the resistance gene were identified and cloned. The sequences for the promoters are set forth in SEQ ID NO: 1 and SEQ ID NO: 2. The method for their isolation is described below.

EXAMPLE 1

Isolation of Promoter Sequences

The procedure for promoter isolation is described in the User Manual for the Genome Walker kit sold by Clontech Laboratories, Inc., Palo Alto, Calif. Genomic DNA from soybean was extracted by grinding 10-day-old seedling leaves in liquid nitrogen, and the DNA prepared according to the following protocol.

Tissue Powdering

1. Add 1.5 mL of glass beads (Fisher 11-312A) and 750 mg (250 mg) dried tissue to a labeled 50 mL (15 mL) polypropylene blue-cap tube. Use a funnel and plunger but do not pack the tissue.

2. Shake tubes in paint shaker for 5 minutes. Reverse the rack and shake the tubes for another 5 minutes.

Cell Disruption

3. In the fume hood combine 2-mercaptoethanol to a final concentration of 1% (v:v) in extraction buffer (1% CTAB, 50 mM Tris-HCl pH 8.0, 0.7 M NaCl, 10 mM EDTA pH 8.0).

4. Add 20 mL (8.5 mL) of extraction buffer per tube.

5. Vortex briefly to mix.

6. Set the mixture at 65° C. for 60 minutes, mixing once or twice during the process by gentle inversion.

Chloroform Wash

7. In the fume hood add 15 mL (5 mL) of chloroform:octanol (24: 1) to each tube. Mix the tubes by doing repeated manual inversions for 5 minutes. A nearly complete emulsion should form.

8. Centrifuge at 2,700 rpm for 30 minutes.

CTAB:DNA Precipitation

9. Add 25 mL (12 mL) precipitation buffer (1% CTAB, 50 mM Tris-HCl pH 8.0, 10 mM EDTA pH 8.0) to a new labeled 50 mL (30 µL) tube.

10. Remove floating stem pieces from the aqueous phase using large forceps; and pour the aqueous phase of the DNA extract into the tube with precipitation buffer.

11. Mix the aqueous material thoroughly by several gentle inversions.

12. Set at room temperature for at least 30 minutes (two hours maximum) to precipitate the CTAB:DNA complex.

13. Centrifuge at 2,700 rpm for 20 minutes.

14. Gently pour off and discard the supernatant.

15. Drain the tubes.

DNA Cleaning

16. Add 2 mL (1 mL) 1 M NaCl to the pellet.

17. Cap and shake the tubes at 65° C., 200 rpm, for 2–3 hours or longer until the pellets are completely dissolved.

18. Add 4.5 mL (2.25 mL) ice cold 95% EtOH. Mix by gently inverting tubes.

19. Set the tubes at −20° C. for 30 minutes or longer (overnight is okay).

20. Spool out the DNA with a glass hook.

21. Place the hooked DNA in 1 mL 65% EtOH for 10 minutes or longer to remove salts.

22. Place the hooked DNA in 1 mL 85% EtOH for 5 minutes or longer to raise the EtOH concentration and further remove salts.

23. Stand the hook on end for 5 minutes or longer to dry the DNA.

24. Place the hooked DNA in 500–1,000 μL (500 μL) TE (10.1). After a few minutes shake the DNA from the hook, remove the hook, and cap the tube.

25. Store at 4° C. until the DNA is dissolved and quantified. Dilute the DNA to 550 ng DNA per μL TE. Store at −20° C. thereafter.

The DNA was then used exactly as described in the Genome Walker User Manual (Clontech PT3042-1 version PR68687). Briefly, the DNA was digested separately with restriction enzymes DraI, EcoRV, PvuII, ScaI, and StuI, all blunt-end cutters. The Genome Walker adapters were then ligated onto the ends of the restricted DNA. The resulting DNA is referred to as DL1-DL5, respectively.

Isolation of the Promoter Region

Additional upstream sequence was then obtained by conducting two rounds of walking using the Genome Walker kit (ClonTech, Palo Alto, Calif.) and genomic DNA from P1437.654, a plant resistant to all known races of soybean cyst nematode. Primer sequences used during the first round of the Genome Walker technique are given in SEQ ID NOs: 3–4. Primer sequences used during the second round are also given in SEQ ID NOs: 5–6. 1168 bp upstream of the translational start codon were obtained. Multiple clones were sequenced at each stage to eliminate PCR errors.

Structural Indications

There are AT rich regions centered approximately 13 and 28 bp upstream of the proposed translational start, one of which may constitute a TATA box. There is a CCAAT sequence 59–63 bp upstream of the proposed translational start that may constitute a CAT box (consensus CCAAT).

The cyst nematode resistant genotypes resistant to some or all races of SCN including P1437.654 (all known), Hartwig, Peking (races 1, 2, 3, 5, 14), Peking (races 1, 3, 5) and P9234 (races 1, 3, 5) have a CCAAT sequence at the proposed CAT box, whereas some susceptible genotypes have a CCCAT sequence here. These susceptible genotypes also have single nucleotide polymorphisms 18, 606, and 993 bp upstream of the translational start codon, single bp deletions 705 and 984 bp upstream of the start, and a 55 bp deletion 935–880 bp upstream of the start, in comparison to the resistant genotypes listed.

EXAMPLE 2

Expression Data Using Promoter Sequences of the Present Invention

A transient expression assay is used to test the cloned DNAs for promoter activity. Each promoter sequence is recloned into a GUS expression vector (FIG. 1). Plasmid DNA is bombarded into maize immature embryos and GUS activity is measured, using the ubiquitin promoter as a control, by counting blue spots after staining for GUS activity as previously described (Jefferson (1987) *Plant Mol. Biol. Rep.* 5:387–405).

EXAMPLE 3

Transformation of Soybean Cells and Regeneration of Transgenic Plants Expressing a Heterologous Gene of Interest Initiation and Maintenance of Embryogenic Suspension Cultures Embryogenic suspension cultures of soybean (Glycine max Merrill) are initiated and maintained in a 10A40N medium supplemented with 5 mM asparagine as described previously (Finer and Nagasowa (1988) *Plant Cell. Tissue Org. Cult.* 15:125–136). For subculture, two clumps of embryogenic tissue, 4 mm in diameter, are transferred to 35 ml of 10A40N medium in a 125-ml deLong flask. High quality embryogenic material is selectively subcultured monthly at this low inoculum density.

Preparation of DNA and Tungsten Pellets

Figure 2:
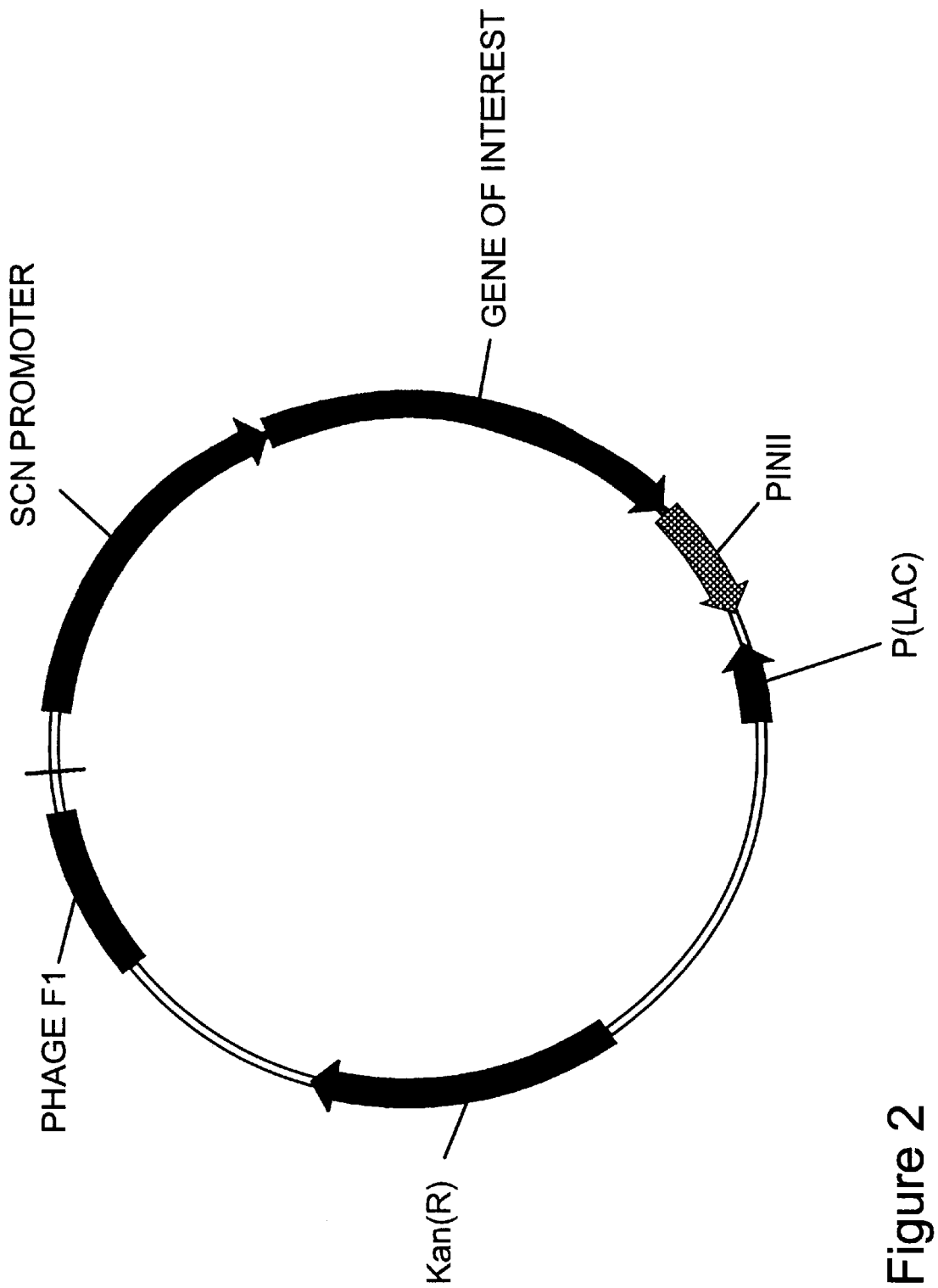
FIG. 2 schematically illustrates the plasmid vector comprising a gene of interest operably linked to a promoter of the present invention.

A plasmid vector comprising a heterologous gene of interest operably linked to a promoter sequence of the present invention is constructed. An expression cassette containing a heterologous gene of interest operably linked to the promoter sequence set forth in SEQ ID NO: 1 or SEQ ID NO: 2 is cloned into a transformation vector (FIG. 2) comprising a kanamycin resistance selectable marker gene.

Plasmid DNA is precipitated onto 1.1 μm (average diameter) tungsten pellets using a $CaCl_2$ precipitation procedure (Finer and McMullen (1990) *Plant Cell Rep.* 8:586–589). The pellet mixture containing the precipitated DNA is gently resuspended after precipitation, and 2 μl is removed for bombardment.

Preparation of Plant Tissue for Bombardment

Approximately 1 g of embryogenic suspension culture tissue (taken 3 wk after subculture) is transferred to a 3.5-cm-diameter petri dish. The tissue is centered in the dish, the excess liquid medium is removed with a pipette, and a sterile 500 μm pore size nylon screen (Tetko Inc., Elmsford, N.Y.) is placed over the embryonic tissue. Open petri dishes are placed in a laminar-flow hood for 10 to 15 minutes to evaporate residual liquid medium from the tissue. The 3.5-cm petri dish is placed in the center of a 9-cm-diameter petri dish immediately before bombardment. Bombardments are performed using a DuPont Biolistics Particle Delivery System (model BPG). Each sample of embryogenic soybean tissue is bombarded once.

Selection for Transgenic Clones

Bombarded tissues are resuspended in the 10A40N maintenance medium. One to two weeks after bombardment the clumps of embryogenic tissue are resuspended in fresh 10A40N medium containing a selection agent, such as kanamycin or hygromycin. The selection agent is filter-sterilized before addition to liquid medium. The medium containing a selection agent is replaced with fresh antibiotic-containing medium weekly for 3 additional weeks.

Six to eight weeks after the initial bombardment, brown clumps of tissue that contain yellow-green lobes of embryogenic tissue are removed and separately subcultured in 10A40N medium containing selection agent. After 3 to 4 months of maintenance in this medium, proliferating embryogenic tissues are maintained by standard subculture in 10A40N without added antibiotic. Embryogenic tissues are periodically removed from 10A40N medium containing selection agent and 10A40N for embryo development and Southern hybridization analyses.

Embryo Development and Germination

For embryo development, clumps of kanamycin-resistant embryogenic tissues are placed at 23° C. on the embryo development medium, which contains MS salts (Murashige and Skoog (1962) *Physiol. Plant* 15:474–497); B5 vitamins (Gamborg et al. (1968) *Exp. Cell Res.* 50:151–158), 6% maltose, and 0.2% gelrite (pH 5.7). One month after plating, the developing embryos are cultured as individual embryos, 25 per 9-cm-diameter petri dish in fresh embryo development medium. After an additional 4 weeks, the mature embryos are placed in dry petri dishes for 2 to 3 days. After the desiccation treatment, the embryos are transferred to a medium containing MS salts, B5 vitamins, 3% sucrose, and 0.2% Gelrite (pH 5.7). After root and shoot elongation, plantlets are transferred to pots containing a 1:1:1 mixture of vermiculite, topsoil, and peat, and maintained under high humidity. Plantlets are gradually exposed to ambient humidity over a 2-week period and placed in the greenhouse, where they are grown to maturity and monitored for expression of the heterologous gene of interest.

DNA Extraction and Southern Hybridization Analysis

DNA is extracted from embryogenic tissue and leaves using the CTAB procedure (Saghai-Maroof et al. (1984) *Proc. Natl. Acad. Sci. USA* 81:8014–8018). Digested DNAs are electrophoresed on a 0.8% agarose gel. The DNA in the gels is treated with 0.2 N HCl, twice for 15 minutes, followed with 0.5 M NaOH/0.1 M 1.5 M NaCl, twice for 30 minutes, and finally 1 M $NH_4C_2H_3O_2$/0.1 M NaOH, for 40 minutes. The DNA is transferred (Vollrath et al. (1988) *Proc. Natl. Acad. Sci. USA* 85:6027–6031) to nylon membranes (Zetaprobe-BioRad, Richmond, Calif.) overnight by capillary transfer using 1 M $NH_4C_2H_3O_2$/0.1 M NaOH. The membranes are baked at 80° C. for 2 hours under vacuum and then prehybridized for 4 to 6 hours at 65° C. in 50 mM Tris, pH 8.0, 5× standard saline citrate (SSC), 2× Denhardt's, 10 mM $Na_2EDTA$, 0.2% sodium dodecyl sulfate (SDS), and 62.5 µg/ml salmon sperm DNA.

EXAMPLE 4

Arabidopsis Transformation by Infiltration with Agrobacterium

Growing Arabidopsis Plants

1. Fill 3.5-inch×3.5-inch pots full with soil. Soak the pots with soil in a water bath for at least a couple of hours to ensure that the soil is saturated with water before planting.

2. Put 3–5 seeds on each planting spot on the soil surface. Plant seeds onto 9 spots in a pot with a 3spots×3spots arrangement. Cover the pots with plastic wrap or any other suitable cover to retain moisture.

3. Transfer the pots to 7° C. (4–10° C.) for 3–4 days for a vernalization treatment.

4. Transfer the pots to greenhouse (16 h light/8 h dark, 25° C.). Thin the plants to one plant per spot of planting after germination.

5. When primary inflorescence begins to flower, while most flower buds have not opened yet, the plants are ready for transformation treatment. This may take four weeks depending on the growing conditions and the Arabidopsis ecotypes used.

Vector

Figure 3:
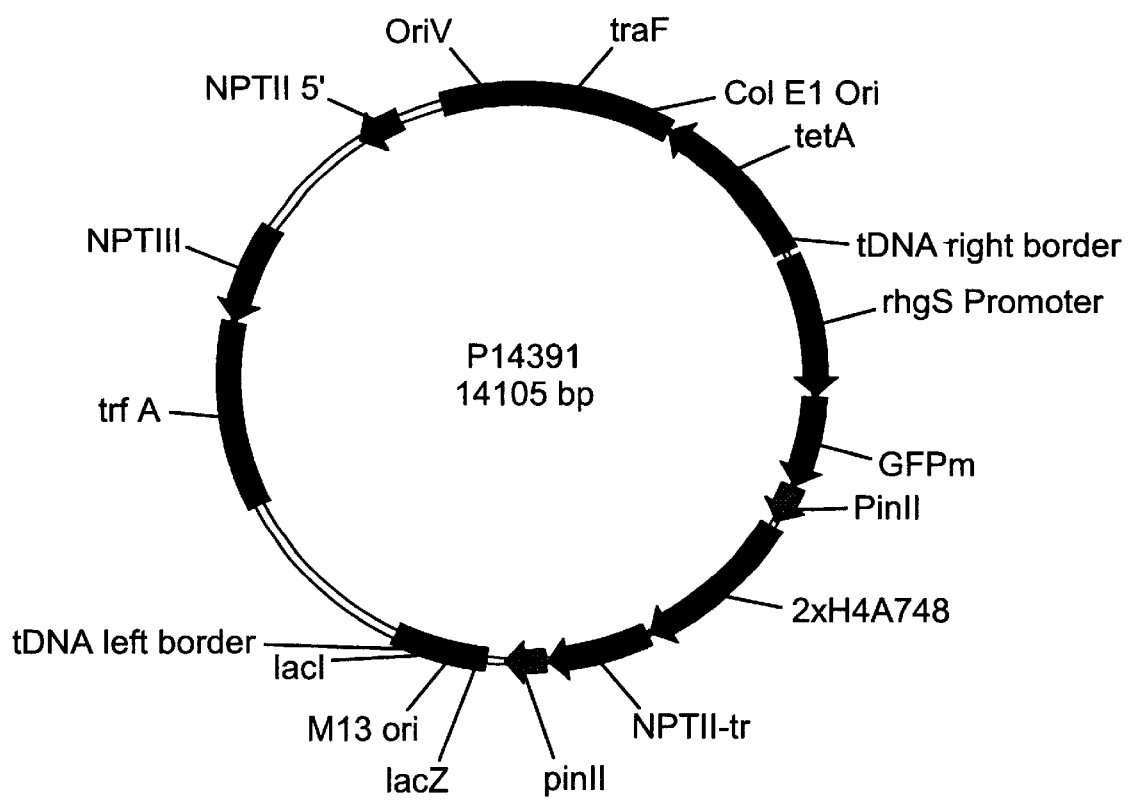
FIG. 3 schematically illustrates a vector for Agrobacterium transformation.

A gene of interest is placed in plasmid P1439 (FIG. 3).

Preparation of Agrobacterium

1. Transfer 3 single colonies from master plate to 20 ml of 810C in a 50-ml flask. Add a suitable antibiotic to 810C medium before use (810C contains no antibiotic; 810B medium contains kanamycin, and 810 medium contains spectinomycin and agar). Incubate the culture at 27° C. overnight with vigorous shaking (200 rpm).

2. In the morning of the second day, transfer 1 ml of the above culture to 500 ml of 810C medium with antibiotic for bulk up culture. Incubate at 27° C. overnight at 200 rpm.

3. On the third day, measure OD600 nm of the culture. When the OD600 nm is around 0.8, the culture is ready for use. Spin down the agrobacteria at 5000 rpm at 4° C. for 10 min using a GS3 rotor of a RC5C centrifuge.

4. Pour out the supernatant from the centrifuge bottles. Add small amount of 700 medium to resuspend the bacterium pellet first, then add more 700 medium to bring the final concentration to $5×10^8$–$1×10^9$ cfe (OD550 nm=0.36–0.72). The Agrobacterium suspension should be used soon after it is prepared in 700 medium.

Infiltration of Arabidopsis Plants with Agrobacterium

1. Fill four 250-ml glass beakers with Agrobacterium suspension. Place the beakers in a vacuum desiccator. Invert the pots with Arabidopsis plants and immerse the plant into the Agrobacterium suspension. Make sure that the flower bolts and the entire rosettes are submerged.

2. Apply vacuum to the desiccator for 20 min. Keep the suction open during the vacuum process.

3. At the end of vacuum infiltration, quickly release the vacuum and transfer the pots with plants to an autoclavable tray. Place the tray in a growth chamber for overnight.

4. On the next day after infiltration, transfer the tray with pots to the greenhouse. Usually, at 4–6 weeks after infiltration treatment the T1 seeds are ready for harvest.

EXAMPLE 5

Transgenic Arabidopsis Screening Protocol

Selection of Resistant Transgenic Plants Containing the Bar Gene by Spraying Plants Growing in Soil with Herbicide 1. Prepare soil in flats for planting of Arabidopsis seeds. Water the soil well to saturation before planting.

2. One hour before planting, spray the soil surface with a fungicide solution (400 mg/L of Banrot), 200 ml/flat or 1 L/5 flats.

3. Dust the Arabidopsis seeds onto the surface of the soil. Cover the flats with plastic wrap.

4. Keep the flats at 7–10° C. for 3–4 days for a vernalization treatment of the seeds.

5. Transfer the flats to greenhouse or growth chamber for germination (16h light/8h dark, 25° C. day/20° C. night). After germination, take off the plastic wrap.

6. Spray the Arabidopsis seedlings once with a fungicide solution once if there is visible fungal growth.

7. At 7–9 days after planting (3 days of vernalization and 4–6 days of germination), start to spray young seedlings with a diluted Liberty herbicide solution containing 10–20 mg/L glufocinate (also known as phosphinothricin). Spray the plants once every other day. It may take 4–5 times of spraying until resistant transgenic plants are identified.

8. Transplant resistant transgenic plants to 3.5-inch×3.5-inch pots for seed production.

Selection of Resistant Transgenic Plants Containing the nptII Gene by Germinating Seeds and Growing Plants on Agar Plates 1. Sterilize Arabidopsis seeds with 50% CLOROX for 10 min. Centrifuge and take out the liquid.

2. Rinse the seeds with autoclaved water three times.

3. Add autoclave water to the amount to dilute the seeds well before planting.

4. Distribute the seeds onto the surface of agar plates containing antibiotic kanamycin (70 mg/L for a low-level selection, 250 mg/L for a moderate/high-level selection).

5. Keep the plates at 7–10° C. for 3–4 days for a vernalization treatment of the seeds.

6. Transfer the plates to light culture room for germination (25° C., 14 h light/10 h dark).

7. The resistant seedlings will be greener and grow faster than the ones that are not resistant.

8. Transfer the resistant seedlings to soil in the greenhouse for seed production.

All publications and patent applications mentioned in the specification are indicative of the level of those skilled in the

What is claimed is:

1. An isolated nucleic acid molecule comprising the nucleotide sequence set forth in SEQ ID NO: 1 or SEQ ID NO: 2.

2. A chimeric gene comprising the nucleic acid molecule of claim 1 operably linked with a heterologous nucleotide sequence.

3. An expression cassette comprising the chimeric gene of claim 2.

4. A transformation vector comprising the expression cassette of claim 3.

5. An isolated nucleic acid molecule comprising at least 200 contiguous nucleotides of the sequence set forth in SEQ ID NO: 1 or SEQ ID NO: 2, wherein said nucleic acid molecule is capable of driving expression of an operably linked heterologous nucleotide sequence in the cells of a plant.

6. A chimeric gene comprising the nucleic acid molecule of claim 5 operably linked with a heterologous nucleotide sequence.

7. An expression cassette comprising the chimeric gene of claim 6.

8. A transformation vector comprising the expression cassette of claim 7.

9. An isolated nucleic acid molecule comprising a nucleotide sequence having at least about 85% sequence identity to the sequence set forth in SEQ ID NO: 1 or SEQ ID NO: 2, wherein said nucleic acid molecule is capable of driving expression of an operably linked heterologous nucleotide sequence in the cells of a plant.

10. A nucleic acid molecule of claim 9 having at least about 90% sequence identity to the sequence set forth in SEQ ID NO: 1 or SEQ ID NO: 2.

11. A chimeric gene comprising the nucleic acid molecule of claim 9 operably linked with a heterologous nucleotide sequence.

12. An expression cassette comprising the chimeric gene of claim 11.

13. A transformation vector comprising the expression cassette of claim 12.

14. A plant stably transformed with a nucleic acid molecule comprising a plant promoter operably linked to a heterologous nucleotide sequence, wherein said plant promoter comprises the nucleotide sequence set forth in SEQ ID NO: 1 or SEQ ID NO: 2.

15. The plant of claim 14, wherein said plant is a dicotyledonous plant.

16. The plant of claim 15, wherein said plant is soybean.

17. The plant of claim 14, wherein said plant is a monocotyledonous plant.

18. The plant of claim 17, wherein said plant is maize.

19. Transformed seed of the plant of any one of claims 14–18.

20. A plant cell stably transformed with a nucleic acid molecule comprising a plant promoter operably linked to a heterologous nucleotide sequence, wherein said plant promoter comprises the nucleotide sequence set forth in SEQ ID NO: 1 or SEQ ID NO: 2.

21. The plant cell of claim 20, wherein said plant cell is from a dicotyledonous plant.

22. The plant cell of claim 21, wherein said plant cell is from soybean.

23. The plant cell of claim 20, wherein said plant cell is from a monocotyledonous plant.

24. The plant cell of claim 23, wherein said plant cell is from maize.

25. A plant stably transformed with a nucleic acid molecule comprising a plant promoter operably linked to a heterologous nucleotide sequence, wherein said plant promoter comprises a nucleotide sequence of at least 200 contiguous nucleotides of the sequence set forth in SEQ ID NO: 1 or SEQ ID NO: 2.

26. The plant of claim 25, wherein said plant is a dicotyledonous plant.

27. The plant of claim 26, wherein said plant is soybean.

28. The plant of claim 25, wherein said plant is a monocotyledonous plant.

29. The plant of claim 28, wherein said plant is maize.

30. Transformed seed of the plant of any one of claims 25–29.

31. A plant cell stably transformed with a nucleic acid molecule comprising a plant promoter operably linked to a heterologous nucleotide sequence, wherein said plant promoter comprises a nucleotide sequence of at least 200 contiguous nucleotides of the sequence set forth in SEQ ID NO: 1 or SEQ ID NO: 2.

32. The plant cell of claim 31, wherein said plant cell is from a dicotyledonous plant.

33. The plant cell of claim 32, wherein said plant cell is from soybean.

34. The plant cell of claim 31, wherein said plant cell is from a monocotyledonous plant.

35. The plant cell of claim 34, wherein said plant cell is from maize.

36. A plant stably transformed with a nucleic acid molecule comprising a plant promoter operably linked to a heterologous nucleotide sequence, wherein said plant promoter comprises a nucleotide sequence having at least about 85% identity to the sequence set forth in SEQ ID NO: 1 or SEQ ID NO: 2.

37. The plant of claim 36 wherein said plant promoter comprises a nucleotide sequence having at least about 90% identity to the sequence set forth in SEQ ID NO: 1 or SEQ ID NO: 2.

38. The plant of claim 36, wherein said plant is a dicotyledonous plant.

39. The plant of claim 38, wherein said plant is soybean.

40. The plant of claim 36, wherein said plant is a monocotyledonous plant.

41. The plant of claim 40, wherein said plant is maize.

42. Transformed seed of the plant of any one of claims 36–41.

43. A plant cell stably transformed with a nucleic acid molecule comprising a plant promoter operably linked to a heterologous nucleotide sequence, wherein said plant promoter comprises a nucleotide sequence having at least about 85% identity to the sequence set forth in SEQ ID NO: 1 or SEQ ID NO: 2.

44. The plant cell of claim 43 wherein said plant promoter comprises a nucleotide sequence having at least about 90% identity to the sequence set forth in SEQ ID NO: 1 or SEQ ID NO: 2.

45. The plant cell of claim 43, wherein said plant cell is from a dicotyledonous plant.

46. The plant cell of claim 45, wherein said plant cell is from soybean.

47. The plant cell of claim 43, wherein said plant cell is from a monocotyledonous plant.

48. The plant cell of claim 47, wherein said plant cell is from maize.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 1692 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Glycine Max (ix) FEATURE:
        (A) NAME/KEY: misc_feature
        (B) LOCATION: 1..1128
        (D) OTHER INFORMATION: /function= "Controls expression of
            resistance gene"
            /product= "Soybean Gene Promoter (Nematode
            Resistance Gene)"

(xi) SEQUENCE DESCRIPTION: SEQ ID NO:1:

```
CGTCTTCTCC AACTTTCTTA GTGTCATTTT GTGACTAGAT CCATTTTGTA AGAAAATAAG      60

ATTAGATTAA AATTATTAAA AAATATCGAG ACTCTCTCAA CTTTTGTTCG ATTTGATTTC     120

TTTTTTTCGT GTGTTATTTT TTTTTGGGGG GTGTGGGTTT GTGTTTGGGA TTGTTTGATT     180

GTTTTGGTTG TTGGTGGAGA AAGGGGAAAG AGAGAGGAAA CAAGAAAGAA AGAGGATAAC     240

AGGACGAGAT TGGCGACGAC GATGACGATT GGGAGAAACC ACAGTCGCAA TGTGTTCGAC     300

TTCCGCGATG GAGCGTTGAT TTTTAAATAA TTCCGACAGG GGAGGTCGTG GGCGTTCCCG     360

TGGCCGGCGA GAGGACAATG CCAAGGGAGT CGCCGGTGCG AATTAGAAAA AAAATAAAAA     420

AAAATACCAG ATATAGAGAA ACAACGACAA AGATTAGTTT GTTTTCCAAT AAAATTACAA     480

GGAAACTTGT TTGTTATTCT TATGAGTAAT TATCTTTTCT ACTGAAGAAA GTTTTGGTTA     540

TGATGTTCAG TTTGCTGGAA CATGAGCTTG GATTGGACTG ACTTAATAAT GATACCCAAA     600

GGAATCTTAG AATCTTAATA TTCTTGTTTT GAGATTAACA AATAAATGTG TGGATTTGTT     660

GAAAAATATG TTCCCCAAAT TTGCTTGCGT CCCTAAGTAC AGCTGGAATT TCTAACTAAT     720

ATTTTCTACG AACCATTAGT TACGGAAGAG ATCACGGTAT ACTAGTGTGG CTGTGGGTAA     780

CAGATGATAT CTAAGTCAAA GAAACTTTCC TATGGTAAAC AAACTACTTC ACTTTCTCAT     840

GCTAGAAGCC GTCTTCTTTA ATTATTACTA TTTACTAGTA CTACTTTCCG TATAATTTTA     900

AATTCATATT TCAAACCACC GCGACTTTCC AATCCCTCGT TCTTCATGCC CCCCAACCCA     960

ACATTCCCAG TCGACACGTC TTCTACTCCT TAATTTCCTC CTTCTTTCAA ACTTGACAAA    1020

GCCACAACTC TTCTCTCATC TCATATAAAT ACCCTTCCAC GACACCAATT TCTCCATCCT    1080

CTCATTGAAA AACAAAATTA ATCATCTTAC TTATTTATTC TCCGAAAATG GTTGATTTAC    1140

ATTGGAAATC AAAGATGCCA AGTTCCGACA TGCCTTCCAA AACTCTAAAA CTCTCTCTCT    1200

CCGACAACAA GTCCTTACCC TCTTTGCAAC TACCCTTCCG CACCACAGAT ATCTCTCACG    1260
```

```
CCGCACCTTC TGTTTGCGCC ACTTACGACT ACTATCTCCG TCTTCCTCAA CTCAGAAAGC    1320

TTTGGAACTC CTCAGATTTT CCTAATTGGA ACAACGAACC AATCTTAAAA CCTATCTTGC    1380

AAGCTCTCGA AATCACCTTC CGCTTTCTCT CCATTGTTCT CTCCGATCCA AGACCTTACT    1440

CCAACCACAG AGAATGGACT CGCAGGATAG AGTCTCTTAT CACACATCAA ATTGAAATCA    1500

TTGCCATACT TTGTGAAGAT GAGGAACAAA ATTCCGACAC ACGTGGCACT GCACCAACCG    1560

CTGATCTCAG CAGGAACAAT AGCAGCGAGA GCAGAAGCTA CAGCGAGGCA AGCCTGCTTC    1620

CGCGGCTTGC CACGTGGTAC AAATCCAAGG ACGTAGCGCA GAGGATCCTT CTCTCAGTTG    1680

AATGCCAAAT GA                                                       1692

(2) INFORMATION FOR SEQ ID NO:2:

(i) SEQUENCE CHARACTERISTICS:
        (A) LENGTH: 1069 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Glycine max (xi) SEQUENCE DESCRIPTION: SEQ ID NO:2:

CGTCTTCTCC AACTTTCTTA GTGTCATTTT GTGACTAGAT CCATTTTGTA AGAAAATAAG      60

ATTAGATTAA AATTATTAAA AAATATCGAG ACTCTCTCAA CTTTTGTTCG ATTTGATTTC     120

TTTTTTTCGT GTGTTGTTTT TTTTGGGGGG TGTGGGTTTG TGTTTGGGAT TGTTTGATTG     180

TTTTGGTTGT TGTTGGCGAC GACGATGACG ATTGGGAGAA ACCACAGTCG CAATGTGTTC     240

GACTTCCGCG ATGGAGCGTT GATTTTTAAA TAATTCCGAC AGGGGAGGTC GTGGGCGTTC     300

CCGTGGCCGG CGAGAGGACA ATGCCAAGGG AGTCGCCGGT GCGAATTAGA AAAAAAATAA     360

AAAAAATACC AGATATAGAG AAACAACGAC AAAGATTAGT TTGTTTTCCA ATAAAATTAC     420

AAGGAAACTT GTTTGTTATT CTTATGAGTA ATTATCTTTT CTACGGAAGA AAGTTTTGGT     480

TATGATGTTC AGTTTGCTGG AACATGAGCT TGGATTGGAC TGACTTAATA ATGATACCCA     540

AAGGAATCTT AGAATCTTAA TATTCTTGTT TTGAGATTAA CAAATAAATG TGTGGATTTG     600

TTGAAAAATA TGTTCCCCAA ATTTGCTTGC GTCCCTAAGT ACAGCTGGAA TTTCTAACTA     660

ATATTTTCTA CGAACCATTA GTTACGGAAG AGATCACGGT ATACTAGTGT GGCTGTGGGT     720

AACAGATGAT ATCTAAGTCA AAGAAACTTT CCTATGGTAA ACAAACTACT TCACTTTCTC     780

ATGCTAGAAG CCGTCTTCTT TAATTATTAC TATTTACTAG TACTACTTTC CGTATAATTT     840

TAAATTCATA TTTCAAACCA CCGCGACTTT CCAATCCCTC GTTCTTCATG CCCCCCAACC     900

CAACATTCCC AGTCGACACG TCTTCTACTC CTTAATTTCC TCCTTCTTTC AAACTTGACA     960

AAGCCACAAC TCTTCTCTCA TCTCATATAA ATACCCTTCC ACGACACCCA TTTCTCCATC    1020

CTCTCATTGA AAAACAAAAT TAATCATCTT ATTTATTTAT TCTCCGAAA              1069

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
```

-continued

```
        (A) DESCRIPTION: /desc = "Synthetic oligonucleotide
            primer"

(xi) SEQUENCE DESCRIPTION: SEQ ID NO:3:

CTCACCCAAA CCCAGCGTGT AGGAACA                                              27

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide
            primer"

(xi) SEQUENCE DESCRIPTION: SEQ ID NO:4:

TCATTTGGCA TTCAACTGAG AGAAGGA                                              27

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide
            primer"

(xi) SEQUENCE DESCRIPTION: SEQ ID NO:5:

GGGCATGAAG AACGAGGGAT TGGAAAG                                              27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide
            primer"

(xi) SEQUENCE DESCRIPTION: SEQ ID NO:6:

CGTGATCTCT TCCGTAACTA ATGGTTC                                              27
```